United States Patent [19]

Lavallee

[11] 4,056,550

[45] Nov. 1, 1977

[54] ALPHA-CYANOETHYLPHTHALATE AND PREPARATION THEREOF

[75] Inventor: Francois A. Lavallee, Willoughby Hills, Ohio

[73] Assignee: General Electric Company, Schenectady, N.Y.

[21] Appl. No.: 680,454

[22] Filed: Apr. 26, 1976

Related U.S. Application Data

[63] Continuation-in-part of Ser. No. 468,405, May 9, 1974, abandoned.

[51] Int. Cl.$^{2}$ .......... C07C 121/66

[52] U.S. Cl. .......... 260/465 D; 260/31.8 K

[58] Field of Search .......... 260/465 D

[56] References Cited

U.S. PATENT DOCUMENTS 2,951,865 9/1960 Jaffe et al. .......... 260/465

*Primary Examiner*—Dolph H. Torrence

*Attorney, Agent, or Firm*—John F. McDevitt; Lawrence R. Kempton; Frank L. Neuhauser

[57] ABSTRACT

This invention relates to a method for preparation of a stereo isomer mixture of crystalline alpha-cyanoethylphthalate wherein the stereo isomer mixture is separated from the reaction mixture by precipitation. More particularly, the stereo isomer mixture is initially formed by reacting lactonitrile and a phthalic acid halide in an organic liquid solution at ambient conditions and the stereo isomer mixture precipitated therefrom by adding an organic precipitant liquid to the reaction mixture. By-products and side-reaction products can be washed from the reaction mixture prior to precipitation of the stereo isomer mixture to provide an alpha-cyanoethylphthalate product having greater purity than conventionally obtained. Additionally, the present alpha-cyanoethylphthalate composition can be characterized as a mixture of the meso and dl isomers wherein one isomer has a predominant weight ratio in the mixture.

15 Claims, No Drawings

ALPHA-CYANOETHYLPHTHALATE AND PREPARATION THEREOF

This application is a continuation-in-part of now abandoned Application Ser. No. 468,405, filed May 9, 1974, and assigned to the assignee of the present invention.

BACKGROUND OF THE INVENTION

Both alpha and beta cyanoethylphthalates are known and have provided a useful class of chemical compounds in a variety of applications including plasticizers. These compounds have been prepared by reacting lactonitrile and hydracrylonitrile with phthaloyl halides in the presence of pyridine. Various methods are also known for preparation of these chemical compounds and which have included complicated processing steps when a purified product was desired. Extraction of the contaminant from the reaction mixture was ordinarily employed followed by distillation of the purified mixture to provide the final product.

The particular extraction procedure heretofore employed for alpha-cyanoethylphthalate purification was both lengthy and involved. Individual extraction steps were conducted in packed columns with deionized water, sulfuric acid, potassium carbonate, and saturated salt solutions, with the extraction schedule further involving repetition of earlier employed extraction liquids. The final extract obtained in this manner was an organic liquid solution of purified alpha-cyanoethylphthalate from which by-products and side-reaction products as well as unreacted starting compounds had been removed. The purified product was separated from the extract solution by a two-step method which involved several evaporations of the organic liquid solvent followed by distillation of the stripped mixture in a molecular still.

A simpler purification method for alpha-cyanoethylphthalate preparation to reduce the processing steps as well as the equipment employed would be desirable.

SUMMARY OF THE INVENTION

It has now been found, surprisingly, that a novel stereo isomer mixture of crystalline alpha-cyanoethylphthalate having a refractive index of about $1.5349n_D^{21°}$ and a melting point in the range from about 62° C to about 66° C can be obtained as a precipitate from the reaction mixture. Basically, the present purification method can be carried out by washing the reaction mixture with a basic aqueous solution and water rinsing in volumes equal to the total reaction mixture for removal of contaminants, stripping organic liquid solvent from the reaction mixture by evaporation at atmospheric pressure, and finally precipitating the purified product from the residual reaction mixture with a suitable organic precipitant liquid. The washing procedure of the present method can produce an essentially contaminant-free product as measured by thin layer chromatography with dilute caustic solution being employed about two or three times and deionized water rinses being used about twice. A wiped film evaporator can be employed for stripping the organic liquid solvent, such as chloroform, from the purified reaction mixture before the product precipitation step is carried out. Suitable organic precipitant liquids to effect physical separation of the purified product from the residual reaction mixture can be selected from the group consisting of primary alcohols, isopropanol, amyl acetate, methylene chloride, ethylene glycol monoethyl ether acetate, xylene, ethyl acetate, acetone, toluene, ethylene glycol monoethyl ether, hexane and other short chain hydrocarbons, petroleum ethers, denatured ethanol and naphtha.

A reaction mixture for purification in accordance with the present invention is prepared in conventional fashion from an organic liquid solution containing approximately stoichiometric quantities of lactonitrile and a phthalic acid halide compound, preferably phthaloyl chloride, and which further contains an amine such as pyridine to form a hydrochloride adduct along with the desired alpha-cyanoethylphthalate reaction product. In this manner, complicated side reactions can be avoided which would make purification of the desired product more difficult and the exothermic reaction is preferably carried out in organic solvents such as chloroform or toluene at relatively high yields upon simple mixture of the reactants at ambient conditions. After initial reaction has taken place, the reaction mixture can be refluxed for complete reaction, but it has been found that initiation of the reaction at reflux temperatures produces certain undesirable results. Lower product yields and more difficulty in product purification were experienced when the reaction was initiated at refluxing temperatures in both chloroform and toluene solvents. The present purification method is carried out with this reaction mixture.

The purified alpha-cyanoethylphthalate product obtained in accordance with the above defined general method can be characterized as a novel stereo isomer mixture of the meso and dl isomers in which one of said isomers predominates. More particularly, the isomer mixture contains approximately 80% by weight of the predominant isomer and about 20% by weight of the other isomer which produces a higher and more narrow melting point range than is obtained by the conventional method wherein said isomers are present in approximately equal proportions. The present method of purification is believed responsible at least in part for such unequal distribution of isomers in the final product since the purification is carried out at lower temperatures than experienced when the product is distilled from the reaction mixture. In this regard, the evaporation step presently being utilized to strip the organic solvent from the washed reaction mixture can be conducted at lower temperatures than are attained in product distillation. The more elevated temperatures experienced in product distillation are believed to enhance a thermodynamic conversion of the isomer ratio to an equal part mixture.

DESCRIPTION OF THE PREFERRED EMBODIMENTS

In one of its preferred embodiments, the reaction mixture can be prepared in a two-step method wherein lactonitrile and a tertiary amine are dissolved in a low molecular weight chlorinated hydrocarbon solvent to form a first solution. A stoichiometric amount of the phthalic acid halide compound for reaction with lactonitrile can be dissolved separately in the same solvent to form a second solution. Chemical reaction is initiated by mixing the two solutions at ambient conditions whereupon alpha-cyanoethylphthalate is formed directly in the reaction mixture as a dissolved product with yields of around 80%. The reaction mixture is refluxed preferably to insure complete reaction. The reaction mixture can then be washed with an aqueous 10% by weight caustic solution and rinsed with water in volumes approximately equal to the total reaction mixture volume. After washing and rinsing, the reaction mixture can be analyzed with thin layer chromatography to determine an acceptable degree of product purification from removal of the by-products, side-reaction products, and residual starting materials. Approximately 85% of the organic liquid solvent can then be stripped from the reaction mixture at atmospheric pressure in a wiped film evaporator at the boiling temperature of the particular organic liquid solvent. A suitable organic precipitant liquid can then be added to the purified reaction mixture and the resultant solution cooled to approximately 0° C and thereafter allowed to stand without further cooling for a sufficient period of time to accomplish product precipitation which generally occurs in about 1 hour. The precipitate can then be filtered in conventional fashion to yield a stereo isomer mixture of crystalline alpha-cyanoethylphthalate having the unequal isomer ratio and physical properties above defined. Representative examples are given below to more fully describe a complete method of preparation in accordance with the present invention.

EXAMPLE I

Approximately 112.9 grams (1.59 moles) lactonitrile were added with approximately 132.8 grams (1.68 moles) pyridine to approximately 250 ml of dry chloroform in a reaction flask. The reaction flask was equipped with a mechanical stirrer and a dropping funnel to permit addition of the remaining reactant. Accordingly, approximately 170.5 gm (0.84 moles) phthaloyl chloride were mixed with approximately 125 ml of dry chloroform and the mixture placed in the dropping funnel. The phthaloyl chloride solution was added slowly with constant stirring to maintain the reaction temperature near ambient conditions over a time period of approximately 1–1½ hours. At the end of this time period the reactant mixture was refluxed for an additional hour to insure complete reaction. Washing of the reaction mixture in an approximately 10 weight percent caustic solution was carried out along with deionized water rinses as hereinbefore described until only small amounts of contaminants were left in the reaction mixture. Likewise, the purified reaction mixture was stripped of solvent at atmospheric pressure in the manner previously described.

To approximately 10 grams of the purified reaction mixture were added with stirring approximately 1.5 ml of ethanol and the solution first cooled to approximately 0° C and then allowed to stand without further cooling for approximately 1 hour whereupon the purified alpha-cyanoethylphthalate isomer mixture had completely precipitated. The precipitate was then filtered to yield a substantially pure final product.

EXAMPLE II

To approximately 10 grams of the reaction mixture prepared as described in the foregoing Example I was added with stirring approximately 1.5 ml of amylacetate and approximately 1.5 ml of mixed hexanes. The resultant solution was then cooled approximately to 0° C and allowed to stand without further cooling for approximately 1 hour for substantially complete separation of the alpha-cyanoethylphthalate isomer mixture as a precipitate. Conventional filtering of the precipitate yielded an isomer mixture substantially equivalent to that already above described.

The alpha-cyanoethylphthalate molecule has a structural configuration permitting two pair of mirror-image stereoisomers which rotate polarized light equally but in opposite directions and a non-optically active stereoisomer which is not a mirror-image isomer of said optically active isomers. Such number of stereoisomers for ths particular molecule is dictated from having two assymetric carbon atoms oriented so that a plane of symmetry divides the molecule into mirror-image halves. In accordance with further stereochemistry principles, the stereoisomer mixtures generally contain approximately equal proportions of stereoisomers which rotate polarized light in a right direction (called d-isomers) and stereoisomers which rotate polarized light in a left direction (called l-isomers) and such isomer content in the mixture is commonly termed the dl-isomers. An optically inactive mixture consisting of equal parts of mirror-image isomers is termed a racemic mixture. Further inclusion of the non-mirror-image isomer (called meso isomer) in said racemic isomer mixture would not impart optical activity so that other than optical means are required to determine the relative proportions of individual isomers in said isomer mixture.

For this purpose, certain magnetic resonance spectroscopy measurements were carried out to compare the stereoisomer proportions in an isomer mixture prepared according to the prior art with a stereoisomer mixture prepared in accordance with the present invention. The prior art mixture was obtained according to U.S. Pat. No. 2,951,865 wherein a purified oily product was obtained which crystallized slowly to white crystals upon standing and exhibited a 53° - 59° C melting point range. A product prepared in accordance with Example 2 (preceding) provided the isomer mixture employed for comparison. Samples of each material were analyzed by a known carbon-13 nuclear magnetic resonance method with the distance or shift between the resonance absorption peaks for the material being tested and the absorption peaks for a tetramethylsilane standard providing the means to identify relative proportions of certain chemical groups, such as $CH_3$, CN, and COO which are present for the specific stereoisomers in the isomer mixture. The results obtained in this manner for the particular isomer mixtures examined are reported in Table 1 (following) along with a structural formula for the alpha-cyanoethylphthalate molecule to indicate location of the particular chemical groups in said molecule which are being reported:

Table 1

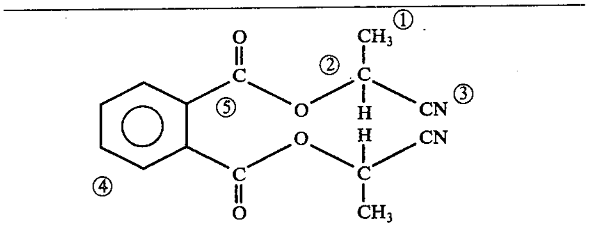

| CHEMICAL GROUP | | RELATIVE ABSORPTION SHIFT Example II Isomer Mixture | Prior Art Isomer Mixture |
|---|---|---|---|
| 1 | $-CH_3$ | 18.7 ppm | 18.6 ppm |
| 2 | —CH— | 59.1 | 59.2 |
| 3 | —CN | 117.80 (30%) | 117.90 (40%) |

Table 1-continued

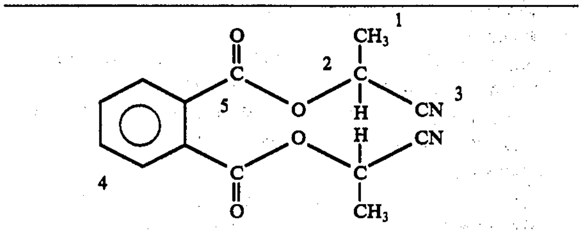

| | CHEMICAL GROUP | RELATIVE ABSORPTION SHIFT Example II Isomer Mixture | Prior Art Isomer Mixture |
|---|---|---|---|
| | | 117.71 (70%) | 117.81 (60%) |
| 4 | Aromatic Carbons | 129.7–132.6 | 129.7–132.6 |
| 5 | 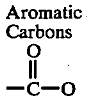 | 165.70 (20%)<br>165.60 (80%) | 165.70 (50%)<br>165.60 (50%) |

The above measurements further include a weight percent rating of the resonance absorption peaks for the CN and COO chemical groups in the dl-isomers and meso isomer present in each isomer mixture analyzed. As can be noted from these absorption peak percentages for the CN group present in these mixtures, there is reported a 30% dl-isomer content and a 70% meso isomer content in the Example 2 isomer mixture whereas the prior art mixture is reported to contain a 40% dl-isomer content and a 60% meso isomer content. The percentages reported for the COO group in said isomer mixtures is regarded as more significant in characterizing the relative proportion of the individual isomers that are present, however, with the Example 2 isomer mixture containing 20% of the dl-isomers and 80% of the meso isomer while the prior art isomer mixture contains approximately equal proportions of said isomers. Consequently, it can be concluded from said measurements that the unexpected improvements previously listed for the novel isomer mixture of the present invention will be obtained when the mixture contains about 80% by weight of the predominant meso isomer and about 20% by weight of the other dl-isomer constituent. Such conclusion is further supported from a recognition that the physical properties of stereoisomers other than mirror-image pairs are not predictable.

It will be apparent from the foregoing description that a purification process for cyanoethylphthalate preparation has been discovered which affords considerable savings in commercial manufacture. It will be appreciated that the invention is not limited to the specific details shown in the examples and illustrations above provided, however, since various modifications may be made within the ordinary skill in the art without departing from the spirit and scope of the present invention. For example, the product can be precipitated from the reaction mixture without cooling if allowed to stand at room temperatures after the precipitant liquid has been added for a longer time period. Consequently, it is intended to limit the present invention only by the scope of the following claims.

What I claim as new and desire to secure by Letters Patent of the United States is:

1. A solid stereo isomer mixture having meso and dl-isomers of crystalline alpha-cyanoethylphthalate with a refractive index of about $1.5349n_D^{21°}$ and a melting point in the range from about 62° C to about 66° C wherein said mixture contains about 80% by weight of the predominant meso isomer and about 20% by weight of the dl-isomers.

2. A method for preparing a solid stereo isomer mixture having meso and dl-isomers of crystalline alpha-cyanoethylphthalate which comprises:

a. reacting lactonitrile and a phthalic acid halide compound in an organic liquid solution containing an amine at ambient conditions to form alpha-cyanoethylphthalate dissolved in the reaction mixture, and b. precipitating the alpha-cyanoethylphthalate as a solid stereo isomer mixture by adding an organic precipitant liquid to the reaction mixture at a temperature whereby said mixture contains about 80% by weight of the predominant meso isomer and about 20% by weight of the dl-isomers, and c. separating the precipitated stereo isomer mixture from the reaction mixture.

3. A method as in claim 2 wherein the reaction mixture is refluxed before precipitation of the alpha-cyanoethylphthalate.

4. A method as in claim 2 wherein the selected phthalic acid halide compound is phthaloyl chloride.

5. A method as in claim 2 wherein the organic precipitant liquid is selected from the group consisting of primary alcohols, isopropanol, amyl acetate, methylene chloride, ethylene glycol monoethyl ether acetate, xylene, ethyl acetate, acetone, toluene, ethylene glycol monoethyl ether, hexane and other short chain hydrocarbons, petroleum ethers, denatured ethanol and naphtha.

6. A method for preparing a solid stereo isomer mixture having meso and dl-isomers of crystalline alpha-cyanoethylphthalate which comprises:

a. dissolving lactonitrile and an amine in a liquid organic solvent to form a first solution, b. dissolving a stoichiometric quantity of a phthalic acid halide compound in the same solvent to form a second solution, c. mixing the solutions at ambient conditions to form alpha-cyanoethylphthalate dissolved in the reaction mixture, d. precipitating the alpha-cyanoethylphthalate as a stereo isomer mixture by adding an organic precipitant liquid to the reaction mixture at a temperature whereby said mixture contains about 80% by weight of the predominant meso isomer and about 20% by weight of the dl-isomers, and separating the precipitated stereoisomer mixture from the reaction mixture.

7. A method as in claim 6 wherein the reaction mixture is refluxed before precipitation of the alpha-cyanoethylphthalate.

8. A method as in claim 6 wherein the selected phthalic acid halide compound is phthaloyl chloride.

9. A method as in claim 6 wherein the organic precipitant liquid is selected from the group consisting of primary alcohols, isopropanol, amyl acetate, methylene chloride, ethylene glycol monoethyl ether acetate, xylene, ethylacetate, acetone, toluene, ethylene glycol monoethyl ether, hexane and other short chain hydrocarbons, petroleum ethers, denatured ethanol and naphtha.

10. A method as in claim 6 wherein the liquid organic hydrocarbon solvent is selected from the group consisting of short chain aliphatic hydrocarbons, halogenated short chain aliphatic hydrocarbons, aromatic hydrocarbons, and halogenated aromatic hydrocarbons.

11. A method as in claim 6 wherein the reaction mixture is washed with a basic solution before precipitation.

12. A method as in claim 6 wherein the liquid organic hydrocarbon solvent is removed from the washed reaction mixture before precipitation.

13. A method as in claim 6 wherein the liquid organic hydrocarbon solvent is removed by evaporation at elevated temperatures.

14. A method for preparing a solid stereo isomer mixture having meso and dl-isomers of crystalline alpha-cyanoethylphthalate which comprises:

a. dissolving lactonitrile and pyridine in a liquid organic solvent to form a first solution, b. dissolving a stoichiometric quantity of phthaloyl chloride in the same solvent to form a second solution, c. mixing the solutions at ambient conditions to form alpha-cyanoethylphthalate dissolved in the reaction mixture, d. washing the reaction mixture with a basic aqueous solution for removal of contaminants, e. removing organic liquid solvent from the washed reaction mixture by evaporation at atmospheric pressure, f. precipitating the alpha-cyanoethylphthalate as a stereoisomer mixture by adding an organic precipitant liquid to the remaining reaction mixture at a temperature whereby said mixture contains about 80% by weight of the predominant meso isomer and about 20% by weight of the dl-isomers, and g. separating the precipitated stereoisomer mixture from the reaction mixture.

15. A method as in claim 14 wherein the reaction mixture is cooled below ambient temperature when the organic precipitant liquid is added.

* * * * *